United States Patent
Bar-Am (10) Patent No.: US 9,750,634 B2
(45) Date of Patent: Sep. 5, 2017

(54) INTRA UTERINE DEVICE

(75) Inventor: Ilan Bar-Am, Jerusalem (IL)

(73) Assignee: OCON MEDICAL LTD (IL)

( * ) Notice: Subject to any disclaimer, the term of this patent is extended or adjusted under 35 U.S.C. 154(b) by 238 days.

(21) Appl. No.: 13/144,624

(22) PCT Filed: Jan. 14, 2010

(86) PCT No.: PCT/IL2010/000035
§ 371 (c)(1),
(2), (4) Date: Jul. 14, 2011

(87) PCT Pub. No.: WO2010/082197
PCT Pub. Date: Jul. 22, 2010

(65) Prior Publication Data
US 2011/0271963 A1    Nov. 10, 2011

Related U.S. Application Data

(60) Provisional application No. 61/145,558, filed on Jan. 18, 2009.

(51) Int. Cl.
*A61F 6/14* (2006.01)
*A61B 17/12* (2006.01)
(Continued)

(52) U.S. Cl.
CPC ........ *A61F 6/142* (2013.01); *A61B 17/12022* (2013.01); *A61B 17/12099* (2013.01);
(Continued)

(58) Field of Classification Search
CPC ................................... A61F 6/14; A61F 6/142
(Continued)

(56) References Cited

U.S. PATENT DOCUMENTS 2,176,559 A * 10/1939 Meckstroth .................. 128/839
3,490,446 A * 1/1970 Stanislav et al. ............. 128/839
(Continued)

FOREIGN PATENT DOCUMENTS

DE    102004061823         7/2006
DE    102004061823 A1 *   7/2006  ............... A61F 6/14
(Continued)

OTHER PUBLICATIONS

DE 102004061823 Machine Translation.*
(Continued)

*Primary Examiner* — Kari Rodriquez
(74) *Attorney, Agent, or Firm* — Wilson Sonsini Goodrich & Rosati (57) ABSTRACT

The present invention discloses an Intra Uterine Ball (IUB) device useful for a gynecological procedure or treatment. The aforesaid device comprises a hollow sleeve for at least partial insertion into the uterine cavity; and, an elongate conformable member with at least a portion comprised of shape memory alloy. The elongate member is adapted to be pushed out from said sleeve within said uterine cavity. It is the core of the invention that the elongate member is adapted to conform into a predetermined three dimensional ball-like configuration within said uterine cavity following its emergence from said sleeve, such that expulsion from said uterine cavity, malposition in said uterine cavity, and perforation of the uterine walls is prevented.

10 Claims, 4 Drawing Sheets

(51) Int. Cl.
A61B 17/42 (2006.01)
A61B 17/00 (2006.01)
(52) U.S. Cl.
CPC ........ *A61B 17/12145* (2013.01); *A61B 17/42* (2013.01); *A61B 2017/00867* (2013.01); *A61B 2017/1205* (2013.01)
(58) Field of Classification Search
USPC ................. 128/830–833, 839–840; 606/191, 606/193–194, 285, 530
See application file for complete search history.

(56) References Cited

U.S. PATENT DOCUMENTS

| | | | |
|---|---|---|---|
| 3,620,212 A | 11/1971 | Fannon, Jr. et al. | |
| 3,789,838 A * | 2/1974 | Fournier et al. | 128/839 |
| 3,810,456 A | 5/1974 | Karman | |
| 3,905,360 A * | 9/1975 | Zaffaroni | 128/833 |
| 3,957,042 A | 5/1976 | Krzaklewski et al. | |
| 3,973,560 A | 8/1976 | Emmett | |
| 4,111,196 A * | 9/1978 | Emmett | 128/833 |
| 4,738,667 A * | 4/1988 | Galloway | 604/530 |
| 2005/0171569 A1* | 8/2005 | Girard et al. | 606/193 |
| 2006/0213522 A1* | 9/2006 | Menchaca et al. | 128/833 |
| 2007/0175536 A1* | 8/2007 | Monetti | A61B 17/12022 140/102.5 |
| 2008/0245371 A1 | 10/2008 | Gruber | |
| 2008/0249534 A1 | 10/2008 | Gruber et al. | |

FOREIGN PATENT DOCUMENTS

| | | |
|---|---|---|
| FR | 1594885 | 6/1970 |
| WO | WO 2010/082197 | 7/2010 |

OTHER PUBLICATIONS

International Search Report and Written Opinion dated Jul. 21, 2010 in corresponding International Application No. PCT/IL2010/000035.
What are the most widely used contraceptive methods across the world?, Births/Birth control, Retrieved on Nov. 16, 2006 at <<http://www.ined.fr/en/everything_about_population/faq/naissances_natalite/bdd/q_text/what_are_the_most_widely_used_contraceptive_methods_across_the_world_/question/80/>>, Institut national d'etudes demographiques (INED).
Maurice, The intrauterine device (IUD)-worth singing about, Progress in Reproductive Health Research, 2002, pp. 1-8, vol. 60, World Health Organization.
Lynch, History of the IUD, Contraception Online, Baylor College of Medicine.
Evolution and Revolution: The Past, Present, and Future of Contraception, Retrieved at <<http://www.contraceptiononline.org/contrareport/article01.cfm?art=93>>, Contraception Online, Baylor College of Medicine, 10 (6), Feb. 2000.
Bradley, Ultrasound Interactive Case Study: Ring IUD, Aug. 1998, Retrieved on Jul. 9, 2006 at <<http://www.obgyn.net/us/us.asp?page=us/present/9808/bradley>>, OBGYN.net.
Kaufman, The cost of IUD failure in China, Studies in Family Planning, May-Jun. 1993, pp. 194-196, 24 (3), Published by Wiley-Blackwell on behalf of the Population Council.
Chapter 2.3: Effectiveness, IUDs—An Update, Dec. 1995, vol. XXIII, No. 5, Population Information Program, Center for Communication Programs, The Johns Hopkins School of Public Health.
Van Kets, Importance of Intrauterine contraception, Contraception Today, Retrieved on Jul. 9, 2006 at <<http://www.contrel.be/IUD%20GENERAL/Mhistory.htm>>, Proceedings of the 4th Congress of the European Society of Contraception, 1997, pp. 112-116, The Parthenon Publishing Group.

Chapter 1: Background, IUDs—An Update, Dec. 1995, vol. XXIII, No. 5, Population Information Program, Center for Communication Programs, The Johns Hopkins School of Public Health.
Delvin, Contraceptive coils (IUDs), Retrieved on Jul. 5, 2006 at <<http://www.netdoctor.co.uk/sex_relationships/facts/contraceptivecoil.htm>>, NetDoctor.co.uk.
French et al., Hormonally impregnated intrauterine systems (IUSs) versus other forms of reversible contraceptives as effective methods of preventing pregnancy, Cochrane Database of Systematic Reviews (3).
Schering, Nova T380 Patient information leaflet (PIL), May 13, 2003, Retrieved on Apr. 27, 2007 at <<http://emc.medicines.org/uk/emc/assets/c/html/displaydoc.asp?documentid=3641>>.
Chapter 2: Types of IUDs, IUDs—An Update, Dec. 1995, vol. XXIII, No. 5, Population Information Program, Center for Communication Programs, The Johns Hopkins School of Public Health.
Smith, Contraceptive Concerns, medpundit: Commentary on medical news by a practicing physician, Mar. 8, 2003, Retrieved on Jul. 16, 2006 at <<http://www.medpundit.blogspot.com/2003_03_02_medpundit_archive.html>>.
Birth Control Options: The Progestasert Intrauterine Device (IUD), 2004, Wyoming Health Council, Retrieved on Jul. 16, 2006 at <<http://wyhc.org/birth_control_options/Progestasert-IUD.php>>.
Chapter 2.5: Bleeding and Pain, IUDs—An Update, Dec. 1995, vol. XXIII, No. 5, Population Information Program, Center for Communication Programs, The Johns Hopkins School of Public Health.
Chapter 2.9: Ectopic Pregnancies, IUDs—An Update, Dec. 1995, vol. XXIII, No. 5, Population Information Program, Center for Communication Programs, The Johns Hopkins School of Public Health.
Mechanisms of the Contraceptive Action of Hormonal Methods and Intrauterine Devices (IUDs), Methods of Contraceptive Action, 2006, Family Health International, Retrieved on Jul. 5, 2006 at <<http://www.fhi.org/en/RH/Pubs/booksReports/methodaction.htm>>.
Keller, IUDs Block Fertilization, Family Health International, Winter 1996, vol. 16, No. 2.
Table 2: Worldwide Use of IUDs, Worldwide Use—Developed Countries, IUDs—An Update, Dec. 1995, vol. XXIII, No. 5, Population Information Program, Center for Communication Programs, The Johns Hopkins School of Public Health.
What are the most widely used contraceptive methods across the world?, Births/Birth control, Retrieved on Nov. 16, 2006 at <<http://www.ined.fr/en/everything_about_population/faq/naissances_natalite/bdd/q_text/what_are_the_most_widely_used_contraceptive_methods_across_the_world_/question/80/>>, Institut national d'etudes demographiques (INED).
The intrauterine device (IUD)-worth singing about, Progress in Reproductive Health Research, 2002, pp. 1-8, vol. 60, World Health Organization.
Chapter 2.3: Effectiveness, IUDs—An Update.
Van Kets, Importance of Intrauterine contraception, Contraception Today, Retrieved on Jul. 9, 2006 at <<http://www.contrel.be/IUD%20GENERAL/Mhistory.htm>>, Proceedings of the 4th Congress of the European Society of Contraception, The Parthenon Publishing Group, 1997, pp. 112-116.
Chapter 1: Background, IUDs—An Update.
Contraceptive coils (IUDs), Retrieved on Jul. 5, 2006 at <<http://www.netdoctor.co.uk/sex_relationships/facts/contraceptivecoil.htm>>, NetDoctor.co.uk.
French et al., Hormonally impregnated intrauterine systems (IUSs) versus other forms of reversible contraceptives as effective methods of preventing pregnancy, Cochrance Database of Systematic Reviews (3).
Chapter 2: Types of IUDs, IUDs—An Update.
Chapter 2.5: Bleeding and Pain, IUDs—An Update.
Chapter 2.9: Ectopic Pregnancies, IUDs—An Update.
Mechanisms of the Contraceptive Action of Hormonal Methods and Intrauterine Devices (IUDs), 2006, Family Health International, Retrieved on Jul. 5, 2006 at <<http://www.fhi.org/en/RH/Pubs/booksReports/methodaction.htm>>.

(56) References Cited

OTHER PUBLICATIONS

Table 2: Worldwide Use of IUDs, Worldwide Use—Developed Countries, IUDs—An Update.
Communication Pursuant to Rules 70(2) and 70a(2) EPC Dated Dec. 17, 2013 From the European Patent Office Re. Application No. 10731117.7.
International Preliminary Report on Patentability Dated Jul. 19, 2011 From the International Bureau of WIPO Re. Application No. PCT/IL2010/000035.
International Preliminary Report on Patentability Dated Jul. 28, 2011 From the International Searching Authority Re. Application No. PCT/IL2010/000035.
International Search Report and the Written Opinion Dated Jul. 21, 2010 From the International Searching Authority Re. Application No. PCT/IL2010/000035.
Office Action Dated Feb. 9, 2012 From the Israel Patent Office Re. Application No. 214106.
Office Action Dated Apr. 30, 2013 From the Israel Patent Office Re. Application No. 214106.
Supplementary European Search Report and the European Search Opinion Dated Nov. 28, 2013 From the European Patent Office Re. Application No. 10731117.7.
Translation of Notification of the Office Action Dated Mar. 28, 2013 From the State Intellectual Property Office of the People's Republic of China Re. Application No. 201080012583.X.
Aguilar et al. "Physiological Pathways and Molecular Mechanisms Regulating Uterine Contractility", Human Reproduction Update, 16(6): 725-744, 2010.
Baker et al. "Minimum Intrauterine Pressure Required for Uterine Distention", Journal of the American Association of Gynecologic Laparoscopists, 5(1): 51-53, Feb. 1998. Abstract.
John Hopkins School "Background", Population Information Program, Center for Communication Programs, The John Hopkins School of Public Health, XXIII(5): Chap.1: Background, Population Reports, Series B, No. 6, 1 P., Dec. 1995.
John Hopkins School "Developed Countries", Population Information Program, Center for Communication Programs, The John Hopkins School of Public Health, XXIII(5): Chap.6.2: Developed Countries, Population Reports, Series B, No. 6, 1 P., Dec. 1995.
John Hopkins School "Worlwide Use of IUDs, 1995. Estimated Use Among Married Women of Reproductive Age", Population Information Program, Center for Communication Programs, The John Hopkins School of Public Health, XX111(5): Table 2, Tables for IUDs—An Update, Series J, No. 45, 7 P., Dec. 1995.
Aguilar et al., "Physioloical pathways and molecular mechanisms regulating uterine contractility", Human Reproduction Update, vol. 16, No. 6, pp. 725-744 (2010).
Baker et al., "Minimum intrauterine pressure required for uterine distention", Abstract, J. Am. Gynecol. Laparosc., vol. 5, No. 1, p. 51-3 (1998).
Office Action Dated Aug. 13, 2014 From the Israel Patent Office Re. Application No. 214106 and Its Translation Into English.
Translation Dated Jan. 15, 2015 of Office Action Dated Dec. 4, 2014 From the Israel Patent Office Re. Application No. 214106.
Office Action Dated Dec. 4, 2014 From the Israel Patent Office Re. Application No. 214106.

\* cited by examiner

INTRA UTERINE DEVICE

FIELD OF THE INVENTION

The present invention generally relates to intrauterine devices. More specifically, the present invention relates to intra-uterine devices useful for a gynecological procedure or treatment and to methods of employing said devices.

BACKGROUND OF THE INVENTION

An intrauterine device is a device placed in the uterus, also known as an IUD. The IUD is the world's most widely used method of reversible birth control [1], currently used by nearly 160 million women, just over two-thirds of whom are in China, where it is the most widely used birth control method [2]. Usage in many countries has been measured by surveys of married women of reproductive age. In this population in the early 1990s, IUD use ranged from 1.5% in North America, to 18% in Scandinavia, 33% in Russia and China, and 40% in Kazakhstan [20]. The use in China has increased to 45% of married women by 2002[2].

The insertion and removal of the IUD into and from the uterus has to be performed by a doctor or qualified medical practitioner. Generally, it remains in place for the entire period of undesired pregnancy. However, practically, depending on the type, a single IUD is approved for 5 to 10 years.

The presence of a device in the uterus prompts the release of leukocytes and prostaglandins by the endometrium. These substances are hostile to both sperm and eggs. It is reported that the presence of copper increases this spermicidal effect [18][19].

Early designed IUDs are coil-shaped based. The first plastic IUD, the Margulies Coil or Margulies Spiral, was introduced in 1958. This device was somewhat large, causing discomfort to a large proportion of women users, and had a hard plastic tail, causing discomfort to their male partners.

The stainless steel single-ring IUD was developed in the 1970s [5] and widely used in China because of low manufacturing costs. The Chinese government banned production of steel IUDs in 1993 due to high failure rates (up to 10% per year) [6] [7].

The plastic T-shaped IUD was conceived in 1968. Shortly thereafter, the idea of adding copper to the devices, in order to improve their contraceptive effectiveness was introduced [3] [8]. It was found that copper-containing devices could be made in smaller sizes without compromising effectiveness, resulting in fewer side effects such as pain and bleeding [9]. T-shaped devices had lower rates of expulsion due to their greater similarity to the shape of the uterus [4].

Second-generation copper-T IUDs were also introduced in the 1970s. These devices had higher surface areas of copper, and for the first time consistently achieved effectiveness rates of greater than 99%. Nevertheless these T-shaped designed IUDs have several drawbacks, causing significant undesirable symptoms to the women.

As is known there are two broad categories of intrauterine contraceptive devices: inert and copper-based devices, and hormonally-based devices that release progestogen.
Non-hormonal IUDs Most of the non-hormonal IUDs have a plastic T-shaped frame that is wound around with pure electrolytic copper wire and/or has copper collars (sleeves). All copper-containing IUDs have a number as part of their name. This is the surface area of copper (in square millimeters) the IUD provides.

In some IUDs, the pure copper wire has a silver core which has been shown to prevent breaking of the wire [10] [12].

The arms of the frame hold the IUD in place near the top of the uterus. The GyneFix does not have a T-shape, but rather is a loop that holds several copper tubes. The GyneFix is held in place by a suture to the fundus of the uterus.

In the following conditions, the insertion of a copper IUD is not usually recommended:
Postpartum between 48 hours and 4 weeks (increased IUD expulsion rate with delayed postpartum insertion)
Benign gestational trophoblastic disease
Ovarian cancer
Very high individual likelihood of exposure to gonorrhea or chlamydial STIs
AIDS (unless clinically well on anti-retroviral therapy)
Cervical cancer (awaiting treatment)
Endometrial cancer
Distortions of the uterine cavity by uterine fibroids or anatomical abnormalities
Current PID
Known pelvic tuberculosis Another disadvantage of the copper IUD concerns women with metal sensitivities to copper or nickel whom may experience adverse reactions from an IUD. The metal used in IUDs is 99.99% copper, with one study finding a maximum nickel content of 0.001%. Because nickel has a relatively high sensitizing potential, a few researchers suggested even this tiny amount might be problematic.

Moreover, after IUD insertion, menstrual periods are often heavier, more painful, or both, especially for the first few months after they are inserted. On average, menstrual blood loss increases by 20-50% after insertion of a copper-T IUD. Increased menstrual discomfort is the most common medical reason reported for IUD removal [16].
Hormonal Intra-Uterine Devices One of the main advantageous of hormonal uterine devices is that they do not increase bleeding as inert and copper-containing IUDs do. Rather, they reduce menstrual bleeding or prevent menstruation altogether, and can be used as a treatment for menorrhagia (heavy periods).

Although use of hormonal intra-uterine devices results in much lower systemic progestogen levels than other very-low-dose progestogen-only hormonal contraceptives, they might possibly have some of the same side effects.

Progestasert was the first hormonal uterine device, developed in 1976[13] and manufactured until 2001[14]. It released progesterone, was replaced annually, and had a failure rate of 2% per year [15].

As of 1997, the LNG-20 IUS—marketed as Mirena by Bayer is the only IntraUterine device available. First introduced in 1990, it releases levonorgestrel (a progestogen) and may be used for five years.

The main side effects and complications of the hormonal IUDs include:
Uterine perforation, especially when the uterine walls are soft or more fragile (after pregnancies, endometritis, adenomyosis etc.). The perforation rate is relatively rare (about 0.5% to about 1%); however, it is probably underestimated due to under reporting.
Expulsion—more common in younger women, women who have not had children, and when an IUD is inserted immediately after childbirth or abortion.
The risk of ectopic pregnancy in pregnancies that do occur during IUD use is higher than the expected percentage (3-4%) [17].

Mal-position of the IUD may increase the rate of undesirable pregnancies. If pregnancy does occur, the presence of the IUD increases the risk of miscarriage, particularly during the second trimester. Even when the IUD is removed in the beginning of the pregnancy, there is still a risk for premature delivery.

The rate of misplacement (the combination of perforation, expulsion and mal-position in the uterus) is at least 3%.

Therefore, it is desirable to have intrauterine devices which overcome the abovementioned drawbacks. There is still a long felt need for IUDs which can be safely and conveniently inserted into the uterine cavity, without causing perforation of the uterine walls. Furthermore, there is still a long felt need to provide IUDs with reduced expulsion and mal-position rates. Such an IUD will reduce the need for unnecessary surgeries and is expected to have less undesirable side effects.

SUMMARY OF THE INVENTION

It is hence one object of the present invention to provide an Intra Uterine Ball (IUB) device useful for a gynecological procedure or treatment, comprising: (a) a hollow sleeve for at least partial insertion into the uterine cavity; and, (b) an elongate conformable member with at least a portion comprised of shape memory alloy, said elongate member is adapted to be pushed out from said sleeve within said uterine cavity, wherein said elongate member is adapted to conform into a predetermined three dimensional ball-like configuration within said uterine cavity following its emergence from said sleeve, such that expulsion from said Uterine cavity, malposition in said uterine cavity, and perforation of the uterine walls is prevented.

It is a further object of the present invention to disclose the IUB as defined above, wherein said elongate member is accommodated within said sleeve prior to insertion into said uterine cavity.

It is a further object of the present invention to disclose the IUB as defined above, wherein at least a portion of said member is configured such that after emergence of said member from said sleeve, said at least a portion is configured in a loop-like shape positioned opposite to the uterine fundus, thereby preventing perforation of the uterine walls.

It is a further object of the present invention to disclose the IUB as defined above, wherein said three dimensional configuration of said member is in a form selected from the group consisting of a ball-like, spherical-like, ovoid-like, globular-like, globe-like, orbicular-like or any other irregular form.

It is a further object of the present invention to disclose the IUB as defined above, wherein said member in its three dimensional configuration has a diameter which is significantly higher than the diameter of the cervical canal thereby expulsion of said member from said uterine cavity is prevented.

It is a further object of the present invention to disclose the IUB as defined above, wherein said member in its three dimensional configuration has a diameter of about 10 mm to about 15 mm.

It is a further object of the present invention to disclose the IUB as defined above, wherein said member is additionally provided with a specialized conformation to facilitate prevention of undesirable side effects selected from the group consisting of perforation of the uterine walls and/or endometrium, expulsion from said uterine cavity, malposition of said member in said uterine cavity and any combination thereof.

It is a further object of the present invention to disclose the IUB as defined above, wherein said conformation is selected from the group comprising of a ball-like, sphere-like, globe-like, spoon-like, oval-like, egg-like, flange-like, lip-like, flattened-like, rounded-like; curved-like, flared-like and a combination thereof.

It is a further object of the present invention to disclose the IUB as defined above, wherein said member comprises an additional section to facilitate prevention of undesirable side effects selected from the group consisting of perforation of the uterine walls and/or endometrium, expulsion from said uterine cavity, malposition of said member in said uterine cavity and any combination thereof.

It is a further object of the present invention to disclose the IUB as defined above, wherein said section comprises material with characteristics selected from the group consisting of soft, resilient, rubbery, elastic and a combination thereof.

It is a further object of the present invention to disclose the IUB as defined above, wherein at least a portion of said member comprises materials or coatings detectable by ultrasound monitoring.

It is a further object of the present invention to disclose the IUB as defined above, wherein at least a portion of said member comprises metal.

It is a further object of the present invention to disclose the IUB as defined above, wherein at least a portion of said member comprises polymeric materials.

It is a further object of the present invention to disclose the IUB as defined above, wherein at least a portion of said member comprises copper.

It is a further object of the present invention to disclose the IUB as defined above, wherein at least a portion of said member is coated with copper.

It is a further object of the present invention to disclose the IUB as defined above, wherein said metal is selected from the group consisting of shape memory alloys, titanium, nickel, nitinol, stainless steel alloys, niobium, zirconium, cobalt-chrome alloys, molybdenum alloys, tungsten-rhenium alloys and any combination thereof.

It is a further object of the present invention to disclose the IUB as defined above, wherein said IUB at least partially comprises elastic materials.

It is a further object of the present invention to disclose the IUB as defined above, wherein said member comprises at its proximal end a sphere-like, conformation.

It is a further object of the present invention to disclose the IUB as defined above, wherein said sphere-like conformation comprises polyethylene and/or silicon materials.

It is a further object of the present invention to disclose the IUB as defined above, wherein said sleeve is adapted to be removed after said pushing out of said member from said sleeve within said uterine cavity.

It is a further object of the present invention to disclose the IUB as defined above, wherein said IUB further comprises insertion means.

It is a further object of the present invention to disclose the IUB as defined above, wherein said insertion means comprise a rod, longitudinally movable in said sleeve, said rod adapted for inserting said elongated member into said uterine cavity.

It is a further object of the present invention to disclose the IUB as defined above, wherein said gynecological procedure or treatment is selected from the group consisting of contraception, fertility treatment and treatment of pelvic inflammatory disease.

It is a further object of the present invention to disclose the IUB as defined above, wherein at least a portion of said member comprises or coated with a drug releasing layer.

It is a further object of the present invention to disclose the IUB as defined above, wherein said drug releasing layer comprises a polymer.

It is a further object of the present invention to disclose the IUB as defined above, wherein said drug releasing layer comprises copper.

It is a further object of the present invention to disclose the IUB as defined above, wherein said drug is in a sustained release form.

It is a further object of the present invention to disclose the IUB as defined above, wherein said drug is in a bolus release form.

It is a further object of the present invention to disclose the IUB as defined above, wherein said IUB facilitates release of said drug into said intrauterine cavity in a uniform manner such that the concentration of said drug in said uterine cavity is uniform, thereby alleviating endometrial bleeding.

It is a further object of the present invention to disclose the IUB as defined above, wherein said drug releasing layer comprises hormones.

It is a further object of the present invention to disclose the IUB as defined above, wherein said drug releasing layer comprises antibiotic agents.

It is a further object of the present invention to disclose the IUB as defined above, wherein said drug releasing layer comprises analgesic agents.

It is a further object of the present invention to disclose the IUB as defined above, wherein said hormone is selected from the group consisting of progestogen, estrogen and a combination thereof.

It is a further object of the present invention to disclose the IUB as defined above, wherein said hormone is a gonadotrophin hormone selected from the group consisting of FSH, a synthetic derivative of FSH, LH, a synthetic derivative of LH and a combination thereof.

It is a further object of the present invention to disclose the IUB as defined above, wherein said drug releasing layer is adapted to release said hormone in a predetermined effective dose for enhancing contraception.

It is a further object of the present invention to disclose the IUB as defined above, wherein said drug releasing layer is further adapted to release said hormone in a predetermined effective dose to reduce symptoms selected from the group consisting of menstrual blood loss in a women having menorrhagia, postmenopausal symptoms and dysmenorrhea symptoms.

It is a further object of the present invention to disclose the IUB as defined above, wherein said drug releasing layer is further adapted to release said hormone in a predetermined effective dose to reduce the menstrual blood loss in women having menorrhagia.

It is a further object of the present invention to disclose the IUB as defined above, wherein said drug releasing layer is adapted to release said hormones in a predetermined effective dose for reducing postmenopausal symptoms.

It is a further object of the present invention to disclose the IUB as defined above, wherein said drug releasing layer is adapted to release said hormones in a predetermined effective dose for reducing dysmenorrhea symptoms.

It is a further object of the present invention to disclose the IUB as defined above, wherein said drug releasing layer is adapted to release said gonadotropin hormones in a predetermined effective dose to induce ovulation.

It is a further object of the present invention to disclose the IUB as defined above, wherein said drug releasing layer is adapted release said antibiotic agent in a predetermined effective dose to prevent pelvic inflammatory disease.

It is a further object of the present invention to disclose the IUB as defined, above, wherein at least a portion of said elongate member, is configured in a predetermined shape analogous to two ring-like or loop-like structures positioned approximately perpendicular or about 90 degrees to each other, so as to form a ball or spherical-like conformation, especially when said at least a portion of said member is fully released from said sleeve. A first loop-like structure defines a plane having top and bottom surfaces and a second loop-like structure extends both over and under the plane defined by the first loop-like structure.

It is another core object of the present invention to provide a method for applying a gynecological procedure or treatment to a subject comprising steps of: (a) obtaining an Intra Uterine Ball (IUB) device, (b) inserting at least a portion of said sleeve into said uterine cavity; and, (c) pushing out said elongate member from said sleeve within said uterine cavity, wherein said elongate member conforms into a predetermined three dimensional ball-like configuration within said uterine cavity following its emergence from said sleeve, thereby preventing expulsion from said uterine cavity, malposition in said uterine cavity and perforation of the uterine walls. The aforesaid IUB comprises: (i) a hollow sleeve; and, (ii) an elongate conformable member with at least a portion comprised of shape memory alloy.

It is a further object of the present invention to disclose the method as defined above, wherein said method further comprises steps of pushing out said elongate member from said sleeve within said uterine cavity, such that said elongate member conforms into a predetermined three dimensional ball-like configuration within said uterine cavity on contact with the uterine fundus.

It is a further object of the present invention to disclose the method as defined above, wherein said method further comprises steps of accommodating said elongate member within said sleeve prior to insertion into said uterine cavity.

It is a further object of the present invention to disclose the method as defined above, wherein said method further comprises steps of configuring at least portion of said member such that after emergence of said member from said sleeve, said at least a portion is configured in a loop-like shape positioned opposite to the uterine fundus, thereby preventing perforation of the uterine walls.

It is a further object of the present invention to disclose the method as defined above, wherein method further comprises steps of configuring said member in a three dimensional configuration in a form selected from the group consisting of a ball-like, spherical-like, ovoid-like, globular-like, globe-like, orbicular-like and irregular form and any combination thereof.

It is a further object of the present invention to disclose the method as defined above; wherein said method further comprises steps of configuring said member in a three dimensional configuration comprising a diameter which is significantly higher than the diameter of the cervical canal thereby preventing expulsion of said member from said uterine cavity.

It is a further object of the present invention to disclose the method as defined above, wherein said method further comprises steps of configuring said member in a three dimensional configuration comprising a diameter of about 10 mm to about 15 mm.

It is a further object of the present invention to disclose the method as defined above, wherein said method further comprises steps of additionally providing said member with a specialized conformation to facilitate prevention of undesirable side effects selected from the group consisting of perforation of the uterine walls and/or endometrium, expulsion from said uterine cavity, malposition of said member in said uterine cavity and any combination thereof.

It is a further object of the present invention to disclose the method as defined above, wherein said method further comprises steps of selecting said conformation from the group consisting of a ball-like, sphere-like, globe-like, oval-like, egg-like, flange-like, lip-like, flattened-like, rounded-like, curved-like, flared-like and any combination thereof.

It is a further object of the present invention to disclose the method as defined above, wherein said method further comprises steps of providing said member with an additional section to facilitate prevention of undesirable side effects selected from the group consisting of perforation, of the uterine walls and/or endometrium, expulsion from said uterine cavity, malposition of said member in said uterine cavity and any combination thereof.

It is a further object of the present invention to disclose the method as defined above, wherein said method further comprises steps of providing said section with a material with characteristics selected from the group consisting of soft, resilient, rubbery, elastic and a combination thereof.

It is a further object of the present invention to disclose the method as defined above, wherein said method further comprises steps of providing at least a portion of said member with materials or coatings detectable by ultrasound monitoring.

It is a further object of the present invention to disclose the method as defined above, wherein said method further comprises steps of providing at least a portion of said member with metal.

It is a further object of the present invention to disclose the method as defined above, wherein said method further comprises steps of providing at least a portion of said member with polymeric materials.

It is a further object of the present invention to disclose the method as defined above, wherein said method further comprises steps of providing at least a portion of said member with copper.

It is a further object of the present invention to disclose the method as defined above, wherein said method further comprises steps of coating at least a portion of said member with copper.

It is a further object of the present invention to disclose the method as defined above, wherein said method further comprises steps of selecting said metal from the group consisting of shape memory alloys, titanium, nickel; nitinol, stainless steel alloys, niobium, zirconium, cobalt-chrome alloys, molybdenum alloys, tungsten-rhenium alloys and any combination thereof.

It is a further object of the present invention to disclose the method as defined above, wherein said method further comprises steps of providing at least partially of said member with elastic materials.

It is a further object of the present invention to disclose the method as definedl above, wherein said method further comprises steps of providing said member at its proximal end with a sphere-like conformation.

It is a further object of the present invention to disclose the method as defined above, wherein said method further comprises steps of providing said sphere-like conformation with polyethylene and/or silicon materials.

It is a further object of the present invention to disclose the method as defined above, wherein said method further comprises steps of removing said sleeve after said pushing out of said member from said sleeve within said uterine cavity.

It is a further object of the present invention to disclose the method as defined above, wherein said method further comprises steps of further providing said IUB with insertion means.

It is a further object of the present invention to disclose the method as defined above, wherein said method further comprises steps of providing said insertion means with a rod, longitudinally movable in said sleeve, said rod adapted for inserting said elongated member into said uterine cavity.

It is a further object of the present invention to disclose the method as defined above, wherein said method further comprises steps of selecting said gynecological procedure or treatment from the group consisting of contraception, fertility treatment and pelvic inflammatory disease.

It is a further object of the present invention to disclose the method as defined above, wherein method further comprises steps of providing or coating at least a portion of said member with a drug releasing layer.

It is a further object of the present invention to disclose the method as defined above, wherein said method further comprises steps of providing said drug releasing layer with a polymer.

It is a further object of the present invention to disclose the method as defined above, wherein said method further comprises steps of providing said drug releasing layer with copper.

It is a further object of the present invention to disclose the method as defined above, wherein said method further comprises steps of formulating said drug in a sustained release form.

It is a further object of the present invention to disclose the method as defined above, wherein said method further comprises steps of formulating said drug release layer in a bolus release form.

It is a further object of the present invention to disclose the method as defined above, wherein said method further comprises steps of facilitating the release of said drug into said intrauterine cavity in a uniform manner such that the concentration of said drug in said uterine cavity is uniform, thereby alleviating endometrial bleeding.

It is a further object of the present invention to disclose the method as defined above, wherein said method further comprises steps of providing said drug releasing layer with hormones.

It is a further object of the present invention to disclose the method as defined above, wherein said method further comprises steps of providing said drug releasing layer with antibiotic agents.

It is a further object of the present invention to disclose the method as defined above, wherein said method further comprises steps of providing said drug releasing layer with analgesic agents.

It is a further object of the present invention to disclose the method as defined above, wherein said method further comprises steps of selecting said hormone from the group consisting of progestogen, estrogen and a combination thereof.

It is a further object of the present invention to disclose the method as defined above, wherein said method further comprises steps of providing said drug releasing layer with a gonadotrophin hormone selected from the group consisting of FSH, a synthetic derivative of FSH, LH, a synthetic derivative of LH and a combination thereof.

It is a further object of the present invention to disclose the method as defined above, wherein said method further comprises steps of releasing said hormone from said drug releasing layer in a predetermined effective dose, thereby enhancing contraception.

It is a further object of the present invention to disclose the method as defined above, wherein said method further comprises steps of releasing said hormone from said drug releasing layer in a predetermined effective dose, thereby reducing or alleviating symptoms selected from the group consisting of menstrual blood loss in a women having menorrhagia, postmenopausal symptoms and dysmenorrhea symptoms.

It is a further object of the present invention to disclose the method as defined above, wherein said method further comprises steps of releasing said hormone from said drug releasing layer in a predetermined effective dose, thereby reducing the menstrual blood loss in women having menorrhagia.

It is a further object of the present invention to disclose the method as defined above, wherein said method further comprises steps of releasing said hormones form said drug releasing layer in a predetermined effective dose for reducing postmenopausal symptoms.

It is a further object of the present invention to disclose the method as defined above, wherein said method further comprises steps of releasing said hormones form said drug releasing layer in a predetermined effective dose for reducing dysmenorrhea symptoms.

It is a further object of the present invention to disclose the method as defined above, wherein said method further comprises steps of releasing said gonadotropin hormones form said drug releasing layer in a predetermined effective dose, thereby inducing ovulation.

It is a further object of the present invention to disclose the method as defined above, wherein said method further comprises steps of releasing said antibiotic agent form said drug releasing layer in a predetermined effective dose, thereby preventing pelvic inflammatory disease.

It is a further object of the present invention to disclose the method as defined above, wherein said method further comprises steps of configuring at least a portion of said elongate member in a predetermined shape analogous to two ring-like or loop-like structures positioned approximately perpendicular or about 90 degrees to each other, so as to form a ball or spherical-like conformation, especially when said least a portion of said member is fully released from said sleeve.

BRIEF DESCRIPTION OF THE DRAWINGS

In order to understand the invention and to see how it may be implemented in practice, a plurality of preferred embodiments will now be described, by way of non-limiting example only, with reference to the accompanying drawings.

FIG. 1 is a schematic illustration demonstrating embodiments of the IUB device positioned inside the uterine cavity, wherein:

FIG. 1B' is a schematic illustration presenting the proximal end of the elongate member pushed out from the sleeve and configured in a loop-like shape, upon contact with the uterine fundus;

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide an Intra Uterine Ball (IUB) device useful for a gynecological procedure or treatment.

The present invention provides an Intra Uterine Ball (IUB) device useful for a gynecological procedure or treatment. The aforementioned IUB device comprises (a) a hollow sleeve 20 for at least partial insertion into the uterine cavity; and, (b) an elongate conformable member 10 with at least a portion comprised of shape memory alloy, adapted to be pushed out from the sleeve 20 within the uterine cavity 60. It is the core aspect of the invention that the elongate member 10 is adapted to conform into a predetermined three dimensional ball-like configuration within said uterine cavity 60 following its emergence from said sleeve, such that expulsion from the uterine cavity, mal-position in the uterine cavity, and perforation of the uterine walls or corpus is prevented.

The currently available IUDs include two main categories: inert and copper-based devices, and hormonally-based devices. Most of these IUDs, from both categories, are in two dimensional forms, specifically, 99% of the current IUDs are in a T-shape or in T-shape variations forms.

The known T-shaped IUDs are reported to have several considerable drawbacks:

1. Perforation of the uterine corpus by the arms or body of the conventional T-shaped IUDs—this undesirable effect may cause pain, infections and bleeding symptoms and therefore a need for surgery in order to remove the IUD.
2. Expulsion after insertion of the IUD—symptoms of partial or complete expulsion include bleeding and/or pain and a risk of undesirable pregnancies.
3. Mal-positioning in the uterus (up side down or transverse)—increasing the risk for pregnancies and protrusion of the sharp ends of the T-shaped IUD arms or body into the uterine walls, causing pain bleeding, purulent discharge, and severe discomfort.
4. Difficulty in ultrasound monitoring, especially referring to the commonly used "Mirena" IUD.

Thus it is a core aspect of the invention to disclose an Intra Uterine Ball (IUB) device which has a novel three dimensional ball-like configuration within the uterine cavity to overcome these problems.

The core invention is embodied as a shape memory, spring-like elongate conformable member housed in a hollow sleeve which is used for at least partial insertion into the uterine cavity. The aforementioned elongate member is conformable into a ball-like structure only after insertion of the device into the uterine cavity and emergence of the elongate member from one end of the sleeve, proximal to the cervix during application. Upon introduction into the uterine cavity, the elongate member is pushed out from the sleeve, allowed to be folded freely into its predetermined three dimensional configuration, having been released from the confines of the sleeve and the confines of the cervical canal.

Thus, since the elongate conformable member is formed from shape memory materials, as soon as it is introduced into the uterine cavity and released from the sleeve confines it conforms into its predetermined three dimensional ball-like final shape.

Figures 1A, 1B:
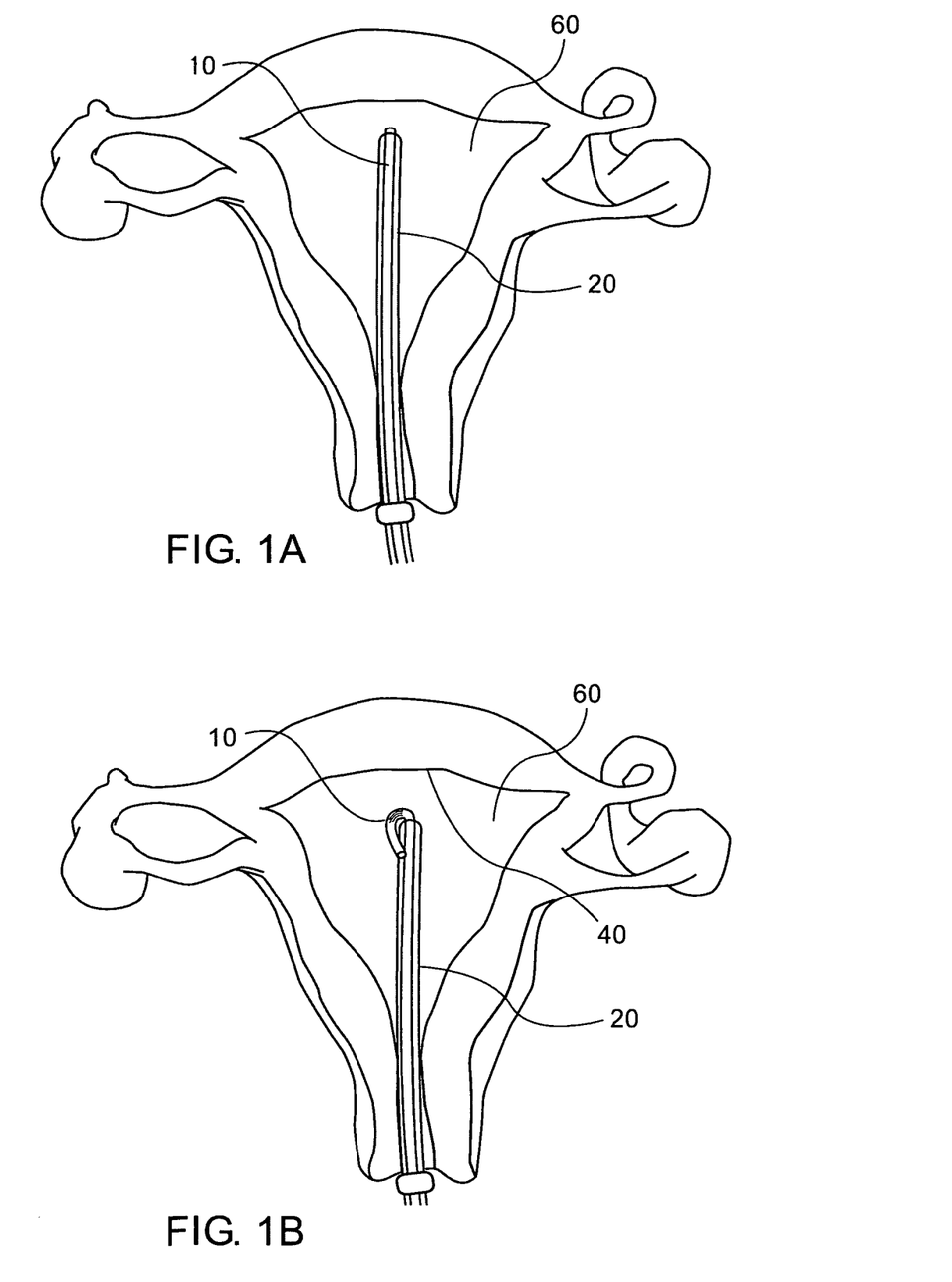
FIG. 1A is a schematic representation of preferred embodiments of the Intra Uterine Ball (IUB) device within the uterus, prior to the emergence of the elongate member from the sleeve confines.
FIG. 1B is a schematic illustration of the IUB device after emergence of the proximal end of the elongate member from the sleeve confines.
Figure 1B:
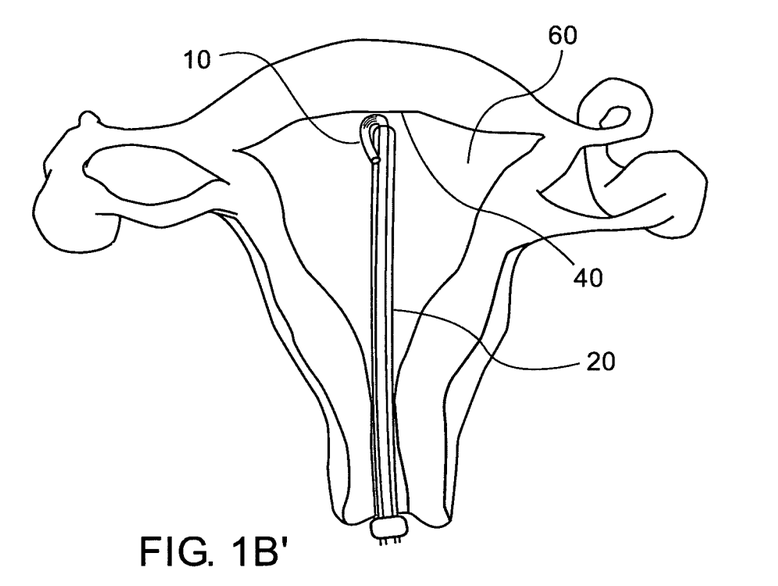

According to another embodiment of the present invention, the elongate member conforms into its predetermined three dimensional ball-like configuration within the uterine cavity on contact with the uterine fundus (FIG. 1B').

It is within the scope of the invention to disclose the elongate conformable member comprising materials having shape memory and elastic properties. These properties enable the aforementioned member to freely conform into its designed three dimensional configuration, when pushed out of the sleeve and introduced into the uterine cavity. In some embodiments of the invention the aforementioned elongate member can be extracted from the sleeve by a special tool or rod designed for the purpose.

In accordance with preferred embodiments of the current invention, the IUB of the present invention comprises a hollow sleeve, and an elongate conformable member accommodated within the sleeve.

It is herein disclosed that the elongate conformable member of the IUB has the ability to fold into a three dimensional configuration after introduction into the uterine cavity and release from the confines of, firstly, the sleeve and secondly the cervical canal. It should be emphasized that the aforesaid ability to deform or conform into a ball like configuration is embodied in the shape memory materials forming the elongated member.

In accordance with a further embodiment of the invention, the elongate member of the IUB is coated with copper or comprises copper for functioning as a conventional copper IUD.

In accordance with another embodiment of the invention the elongate member of the IUB comprises or is covered by a hormone releasing layer for functioning as a hormone releasing IUD.

It is herein acknowledged that the ball-like, three dimensional configuration of the IUB of the current invention encapsulates several advantages which overcome the above mentioned drawbacks of the currently available IUDs:

1. Reduced perforation rate—
    After, insertion into the uterine cavity, the proximal part of the elongate conformable member is pushed out from the sleeve in a predetermined transient configuration (see FIGS. 1A and 1B), wherein the proximal part of the member (FIG. 1B, 10) is bent at about 180°, forming a loop-like shape, positioned opposite the uterine fundus (FIG. 1B, 40). The aforementioned sleeve 20 prevents the shape memory member 10 from assuming it's final ball-like shape prior to insertion into the uterus 60. As the elongate conformable member is pushed from the sleeve, the proximal end begins to assume the final ball-like conformation (see FIGS. 1B and 1C). This specific predetermined transient conformation reduces the risk for perforation of the uterine walls by the IUB, during it's emergence from the cervical canal and introduction into the uterine cavity.

In accordance with preferred embodiments of the invention, the proximal end of the elongate conformable member contains a sphere-like structure (FIG. 1D, 70) to prevent protrusion or perforation of the uterine walls during emergence of the elongate member from the sleeve and its introduction into the uterus. The sphere-like structure consists of elastic and soft materials such as polyethylene and silicon to reduce the risk for perforation.

The ball-like configuration of the shape memory member (see FIGS. 1D, 1E and 1F) is adapted to prevent the protrusion into the uterine corpus caused by the sharp arms of the commonly used T-shaped IUDs, and hence preventing significant discomfort to the user.

2. Reduced expulsion rate—
    The diameter of the shape memory member in its ball-like configuration is significantly wider or higher than the diameter of the cervical canal. Specifically the diameter of the three dimensional ball-like configuration is between about 10 to about 15 mm, which is at least 3 times wider than the diameter of the cervical canal, which is between about 1 to about 4 mm in reproductive aged women.

In uterine contraction conditions the three dimensional spherical configuration can be contracted to a smaller size, however upon relief of the uterine contraction, the spherical or ball-like form expands back to its original or designed size and configuration, which is attributed to the elastic properties of the IUB of the invention.

3. Reduced mal-position rate—
    A ball or spherical configuration, in any of its possible positions has similar dimensions; hence the dimensions of the IUB in its final ball-like configuration significantly reduce the risk for mal-positioning in the uterus.

There are no T wings or arms, as common in the available IUDs to protrude the uterine walls in mal-positioning conditions; hence by using the IUB device, pain discomfort, contractions and abnormal discharge symptoms are prevented.

4. Homogenous hormone release—
    In accordance with a preferred embodiment of the invention, when carrying a drug releasing layer, the three dimensional configuration of the IUB enables the release of a drug, such as a hormone, in three dimensions, and therefore in a less localized manner. The three dimensional release of the drug attributes to its homogenous spread in the uterine space, thereby alleviating bloody spotting symptoms of the endometrial tissue.

5. Detection by ultrasound—
    In accordance with another embodiment of the invention, the IUB is made from materials or coatings detectable by ultrasound. Ultrasound detection swenables monitoring the IUB in the uterine cavity by a qualified medical practitioner and prevents mal-positioning and misplacement events.

In the light of the above detailed advantages, by using the IUB device provided by the present invention, unnecessary surgeries and undesirable pregnancies and discomforts to the user are prevented.

As used herein, the term 'spherical configuration' refers to a symmetrical geometrical configuration. More specifically the term spherical refers to a three dimensional conformation such as a ball-like or globe-like or oval-like or egg-like, spherical-like, ovoid-like, globular-like, orbicular-like shape. The core embodiment is the three dimensional aspect of the invention, and some embodiments may even be irregularly shaped, but nevertheless essentially three dimensional.

The term 'specialized conformation' used herein refers to conformations, structures and shapes of sections and parts that consist within the elongate member in its final configuration and its intermediate forms when introduced into the uterine cavity. These conformations include: ball-like, sphere-like, globe-like, spoon-like, oval-like, egg-like, flange-like, lip-like, flattened-like, rounded-like, curved-like, flared-like shape and a combination thereof.

The term 'sphere like conformation' used herein refers in a non limiting manner to a round shaped marble, bowl, knob, knurl, nodosity and swelling shapes or forms.

The term 'sleeve' used herein refers in a non limiting manner to a tube-like, a cylinder-like, confinement open in its two ends, a tubular shaped or tunnel shaped article.

The term 'filament' used herein refers in a non limiting manner to a thread, a single thread or a thin flexible threadlike object, a fine or thinly spun thread, fiber, or wire.

The term 'shape memory alloy' used herein refers to is an alloy that "remembers" its shape, and can be returned to that shape after being deformed. Shape memory alloys have numerous applications in the medical and aerospace industries. The three main types of shape memory alloys are the copper-zinc-aluminum-nickel, copper-aluminum-nickel, and nickel-titanium (NiTi) alloys.

The term 'about' used hereinafter refers to a range of 10% below or above the referred value.

The term 'biocompatible materials' used hereinafter refers to a synthetic or natural material used to replace part of a living system or to function in intimate contact with living tissue. Biocompatible materials are chemically inert, non toxic, substantially non-immunogenic and non thrombogenic.

The term 'significantly higher' used hereinafter refers to a diameter which is at least about two fold higher than the referred value.

The term 'undesirable side effects' used herein refers to uterine/vaginal bleeding or spotting, pain, contractions and abnormal uterine/vaginal discharge.

The term 'dysmenorrhea' used herein refers to a medical condition characterized by severe uterine pain during menstruation. While most women experience minor pain during menstruation, dysmenorrhea is diagnosed when the pain is so severe as to limit normal activities, or require medication. Dysmenorrhea may be involved with excessively heavy blood loss, known as menorrhagia.

The term 'menorrhagia' or 'hypermenorrhea' used hereinafter refers to an abnormally heavy and prolonged menstrual period or flow at regular intervals. Causes may be due to abnormal blood clotting, disruption of normal hormonal regulation of periods or disorders of the endometrial lining of the uterus. Hypermenorrhea can be a symptom of uterine tumors and can lead to anemia if prolonged.

The term 'postmenopausal symptoms' used herein refers to the effects caused by the extreme fluctuations in hormone levels, especially due to low estrogen levels in the postmenopausal period. The active symptoms of menopause include hot flashes and palpitations, psychological effects such as depression, anxiety, irritability, mood and sleep disturbances, memory problems and lack of concentration, and atrophic effects such as vaginal dryness and urgency of urination. Therefore, postmenopausal hormone therapy, commonly used by women for disease prevention, also affects the quality of life of postmenopausal women.

The term 'proximal part' or 'proximal portion' used herein refers to embodiments of the IUB device of the present invention, more specifically to the end of the elongate member of the IUB device proximal to the cervix, during the application of the device into the uterine cavity. According to preferred embodiments of the invention, this proximal part of the elongate member comprises a sphere-like, shape so as to prevent protrusion to and perforation of the uterine corpus.

According to one aspect of the invention, the IUB comprises or is coated with copper for preventing conception by mechanical means.

According to another aspect of the invention, the IUB comprises or is coated with a drug releasing layer for functioning as a specific drug delivery device useful for a gynecological procedure or treatment. The drugs released from the IUB device include hormones, antibiotic agents and analgesic agents.

The hormones released by the IUB device of the present invention include:
1. progestogen, more specifically progesterone, and estrogen and their combination, that affect the following gynecological conditions:
    a. preventing conception.
    b. hormone replacing therapy for women having symptoms including menorrhagia, hypermenorrhea, dysmenorrhea and postmenopausal associated symptoms.
2. fertility treatment hormones such as FSH and LH and their synthetic derivatives (menotropin—containing gonadotopin hormones) affect ovarian stimulation, thereby inducing fertility.

In accordance with further embodiments of the invention, the IUB device releases antibiotic agents. The antibiotic agents are useful for treatment and/or prevention of Pelvic Inflammatory Disease (PID), including Tubo-Ovarian Abscess (TOA).

Thus according to main aspects of the present invention, the IUB device is used for a gynecological procedure or treatment selected from the group consisting of contraception, fertility treatment and Pelvic Inflammatory Disease (PID) treatment and/or prevention.

It would be beneficial to the subject to use the IUB device for providing the aforementioned drugs directly to the target tissue, namely the uterus, avoiding the inconveniences and problems associated with oral administration such as the 'burst" effect, patient compliance and relatively high systemic doses, while allowing much more direct and higher effectiveness with lower doses of the active agent.

The delivery of the hormone or active ingredient, into the uterine cavity as herein disclosed, is directed close to the target site, increasing bioavailability and is thus less systemic than orally administered drugs or hormone therapies. This method of delivery allows for lower doses that may be given to the patient, whilst maintaining the desirable effect.

Reference is now made to the drawings; FIG. 1 schematically illustrates an Intra Uterine Ball (IUB) device, as a preferred embodiment of the invention. In this diagram the IUB device is positioned within the uterus, wherein numerical reference 10 illustrates the elongate conformable member; 20 is the hollow sleeve accommodating the member and 60 is the uterine cavity. FIG. 1 illustrates the different conformations of the shape memory member 10, from its elongated configuration within the sleeve 20 confines, until it reaches its three dimensional, ball, shaped final configuration. The following stages are presented in FIG. 1:

FIG. 1A schematically illustrates the IUB device within the uterus prior to the emergence of the elongated member from the sleeve confines. As illustrated, the IUB device comprises an elongated member 10 constructed from shape memory materials and adapted for insertion into the uterine cavity 60. The elongated member is accommodated within a sleeve 20. After insertion through the cervical canal and introduction into the uterine cavity 60, and prior to the emergence of the member 10 form the sleeve 20, the shape memory member 10 is accommodated within the sleeve 20, defining it's elongated form (FIG. 1A). As the aforementioned member is pushed out from the sleeve 20, the proximal end of the member begins to assume it's final predetermined ball-like conformation (FIGS. 1B-1F):

Firstly, as demonstrated in FIG. 1B and FIG. 1W the proximal end of the member 10 begins to bent, forming a loop-like shape at a position which is opposite to the uterine fundus 40. Thus FIG. 1B schematically illustrates the IUB device in a transient conformation after insertion into the uterine cavity 60. As illustrated, the elongate member 10 is partially pushed out from sleeve 20. Since the aforesaid member comprises shape memory materials, after introduction into the uterine cavity and extraction of the elongated member from the sleeve confines, the proximal end of the aforesaid member 10 is deformed into a predetermined configuration, wherein the aforesaid proximal end begins to bent at about 180°, forming a loop-like shape, positioned opposite to the uterine fundus 40 and parallel to the uterine walls. This specific position significantly reduces the risk for perforation and penetration the uterine corpus. As illustrated in FIG. 1B', according to embodiments of the invention, the elongate member 10 conforms into its predetermined configuration upon contact with the uterine fundus 40.

Figure 1C:
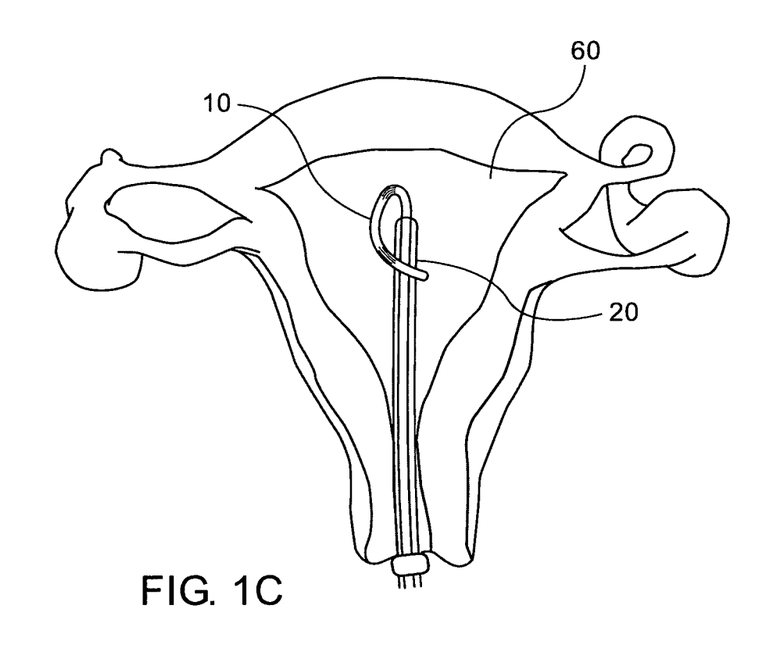
FIG. 1C is a schematic illustration of the elongate member folded into a three dimensional transient configuration.

Than, the conformable shape-memory member is folded into it's three dimensional ball-like configuration through predetermined transient conformations as illustrated in FIG. 1C. It should be emphasized that these transient conformations are adapted to reduce perforation and protrusion risk.

Figure 1D:
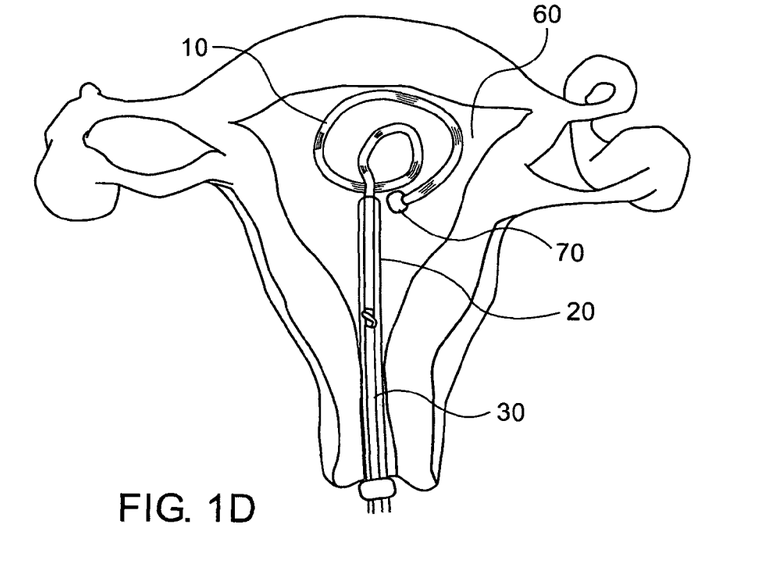
FIG. 1D is a schematic illustration of preferred embodiments of the IUB device in a predetermined three dimensional configuration following introduction of the elongate membrane into the uterine cavity.
Figure 1E:
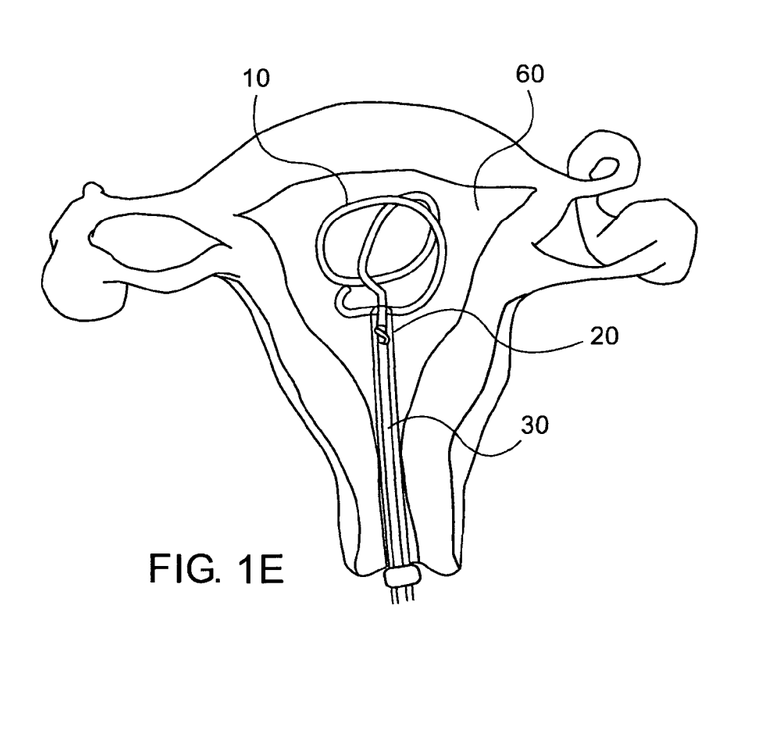
FIG. 1E is an illustration of the elongate member in its predetermined three dimensional, final ball-shape configuration; and, FIG. 1F is a schematic representation of the IUB device fully released in the uterine cavity after the sleeve has been removed.
Figure 1F:
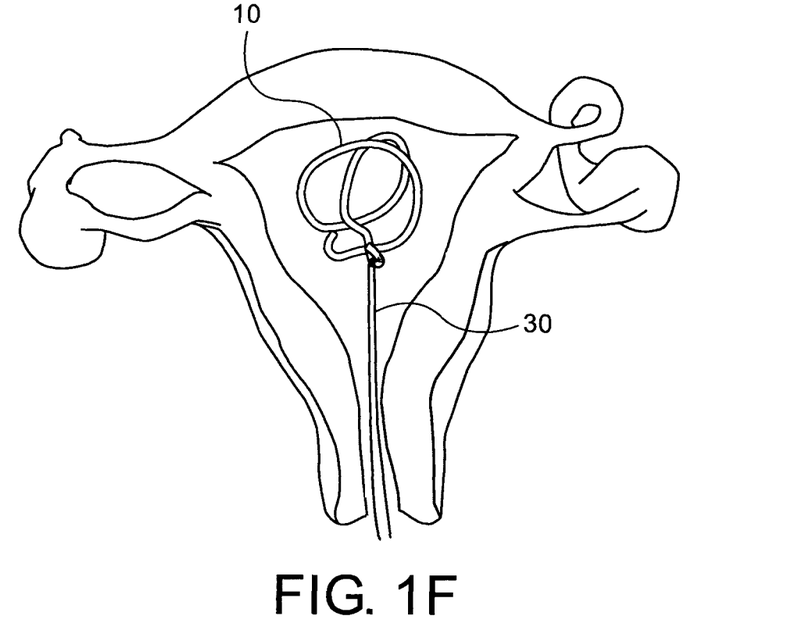

Finally, as illustrated in FIG. 1D-1F, the sleeve is gradually removed and the shape-memory member 10 is fully released in the uterine cavity, assuming its three dimensional ball-like configuration. The aforesaid ball-like or spherical configuration is specifically adapted to prevent perforation, expulsion and/or mal-positioning caused by using the conventional available IUDs.

Reference is now made to FIG. 1D schematically illustrating the conformable member in its predetermined transient three-dimensional configuration. In accordance with a preferred embodiment, the conformable, member comprises a sphere-like shape or structure 70 in its proximal end. This structure 70 is adapted to prevent or reduce protrusion or perforation of the uterine corpus caused by existence of sharp ends of structures. In accordance with additional preferred embodiments of the IUB device, filaments 30 are connected to the caudal end of the elongated member 10.

FIG. 1E schematically illustrates the elongate conformable member 10 in its predetermined, ball-like configuration within the uterine cavity. In accordance with a preferred embodiment of the invention, the elongate member 10, fully released from the sleeve confines, is configured in a predetermined shape configured in a manner analogous to two ring-like or loop-like structures which are positioned approximately perpendicular or about 90 degrees to each other, forming a ball or spherical-like conformation.

FIG. 1F schematically illustrates the elongate conformable member 10 fully released in the uterine cavity after the sleeve 20 has been completely removed. As illustrated, the shape memory member 10, conformed into its predetermined three dimensional configuration, is fully released from the sleeve in the uterine cavity. Filaments 30 are located outside the cervix in order to remove the device when desirable.

Thus, in accordance with the current invention, an Intra Uterine Ball (IUB) device useful for a gynecological procedure or treatment is provided. The aforesaid device comprising:
  a. a hollow sleeve for at least partial insertion into the uterine cavity; and,
  b. an elongate conformable member with at least a portion comprised of shape memory alloy, said elongate member is adapted to be pushed out from said sleeve within said uterine cavity.
  It is the core of the invention that said elongate member is adapted to conform into a predetermined three dimensional ball-like configuration within said uterine cavity following its emergence from said sleeve, such that expulsion from said uterine cavity, malposition in said uterine cavity, and perforation of the uterine walls is prevented.

In accordance with one embodiment of the invention, the aforementioned elongate member is accommodated within said sleeve prior to insertion into said uterine cavity.

In accordance with another embodiment of the invention, at least a portion of said member is configured such that after emergence of said member from said sleeve, said at least a portion is configured in a loop-like shape positioned opposite to the uterine fundus, thereby preventing perforation of the uterine walls.

In accordance with another embodiment of the invention, the aforementioned three dimensional configuration of said member is in a form selected from the group consisting of a ball-like, spherical-like, ovoid-like, globular-like, globe-like, orbicular-like or any other irregular form.

In accordance with another embodiment of the invention, the aforementioned member in its three dimensional configuration has a diameter which is significantly higher than the diameter of the cervical canal thereby expulsion of said member from said uterine cavity is prevented.

In accordance with another embodiment of the invention, the aforementioned member in its three dimensional configuration has a diameter of about 10 mm to about 15 mm.

In accordance with another embodiment of the invention, the aforementioned member is additionally provided with a specialized conformation to facilitate prevention of undesirable side effects selected from the group consisting of perforation of the uterine walls and/or endometrium, expulsion from said uterine cavity, malposition of said member in said uterine cavity and any combination thereof.

In accordance with another embodiment of the invention, the aforementioned conformation is selected from the group comprising of a ball-like, sphere-like, globe-like, spoon-like, oval-like, egg-like, flange-like, lip-like, flattened-like, rounded-like, curved-like, flared-like and a combination thereof.

In accordance with another embodiment of the invention, the aforementioned member comprises an additional section to facilitate prevention of undesirable side effects selected from the group consisting of perforation of the uterine walls and/or endometrium, expulsion from said uterine cavity, malposition of said member in said uterine cavity and any combination thereof.

In accordance with another embodiment of the invention, the aforementioned section comprises material with characteristics selected from the group consisting of soft, resilient, rubbery, elastic and a combination thereof.

In accordance with another embodiment of the invention, at least a portion of said member comprises materials or coatings detectable by ultrasound monitoring.

In accordance with another embodiment of the invention, at least a portion of said member comprises metal.

In accordance with another embodiment of the invention, at least a portion of said member comprises polymeric materials.

In accordance with another embodiment of the invention, at least a portion of said member comprises copper.

In accordance with another embodiment of the invention, at least a portion of said member is coated with copper.

In accordance with another embodiment of the invention, the aforementioned metal is selected from the group consisting of shape memory alloys, titanium, nickel, nitinol, stainless steel alloys, niobium, zirconium, cobalt-chrome allays, molybdenum alloys, tungsten-rhenium alloys and any combination thereof.

In accordance with another embodiment of the invention, the aforementioned IUB at least partially comprises elastic materials.

In accordance with another embodiment of the invention, the aforementioned member comprises at its proximal end a sphere-like conformation.

In accordance with another embodiment of the invention, the aforementioned sphere-like conformation comprises polyethylene and/or silicon materials.

In accordance with another embodiment of the invention, the aforementioned sleeve is adapted to be removed after said pushing out of said member from said sleeve within said uterine cavity.

In accordance with another embodiment of the invention, the aforementioned IUB further comprises insertion means.

In accordance with another embodiment of the invention, the aforementioned insertion means comprise a rod, longitudinally movable in said sleeve, said rod adapted for inserting said elongated member into said uterine cavity.

In accordance with another embodiment of the invention, the aforementioned gynecological procedure or treatment is selected from the group consisting of contraception, fertility treatment and treatment of pelvic inflammatory disease.

In accordance with another embodiment of the invention, at least a portion of said member comprises or coated with a drug releasing layer.

In accordance with another embodiment of the invention, the aforementioned drug releasing layer comprises a polymer.

In accordance with another embodiment of the invention, the aforementioned drug releasing layer comprises copper.

In accordance with another embodiment of the invention, the aforementioned drug is in a sustained release form.

In accordance with another embodiment of the invention, the aforementioned drug is in a bolus release form.

In accordance with another embodiment of the invention, the aforementioned IUB facilitates release of said drug into said intrauterine cavity in a uniform manner such that the concentration of said drug in said uterine cavity is uniform, thereby alleviating endometrial bleeding.

In accordance with another embodiment of the invention, the aforementioned drug releasing layer comprises hormones.

In accordance with another embodiment of the invention, the aforementioned drug releasing layer comprises antibiotic agents.

In accordance with another embodiment of the invention, the aforementioned drug releasing layer comprises analgesic agents.

In accordance with another embodiment of the invention, the aforementioned hormone is selected from the group consisting of progestogen, more specifically progesterone, estrogen and a combination thereof.

In accordance with another embodiment of the invention, the aforementioned hormone is a gonadotrophin hormone selected from the group consisting of FSH, a synthetic derivative of FSH, LH, a synthetic derivative of LH and a combination thereof.

In accordance with another embodiment of the invention, the aforementioned drug releasing layer is adapted to release said hormone in a predetermined effective dose for enhancing contraception.

In accordance with another embodiment of the invention, the aforementioned drug releasing layer is further adapted to release said hormone in a predetermined effective dose to reduce symptoms selected from the group consisting of menstrual blood loss in a women having menorrhagia, postmenopausal symptoms and dysmenorrhea symptoms.

In accordance with another embodiment of the invention, the aforementioned drug releasing layer is further adapted to release said hormone in a predetermined effective dose to reduce the menstrual blood loss in women having menorrhagia.

In accordance with another embodiment of the invention, the aforementioned drug releasing layer is adapted to release said hormones in a predetermined effective dose for reducing postmenopausal symptoms.

In accordance with another embodiment of the invention, the aforementioned drug releasing layer is adapted to release said hormones in a predetermined effective dose for reducing dysmenorrhea symptoms.

In accordance with another embodiment of the invention, the aforementioned drug releasing layer is adapted to release said gonadotrophin hormones in a predetermined effective dose to induce ovulation.

In accordance with another embodiment of the invention, the aforementioned drug releasing layer is adapted release said antibiotic agent in a predetermined effective dose to prevent pelvic inflammatory disease.

In accordance with another embodiment of the invention, at least a portion of said elongate member, is configured in a predetermined shape analogous to two ring-like or loop-like structures positioned approximately perpendicular or about 90 degrees to each other, so as to form a ball or spherical-like conformation, especially when said at least a portion of said member is fully released from said sleeve.

The current invention further discloses a method for applying a gynecological procedure or treatment to a subject comprising steps of:

a. obtaining an Intra Uterine Ball (IUB) device, said IUB comprising:
   i. a hollow sleeve; and,
   ii. an elongate conformable member with at least a portion comprised of shape memory alloy;
b. inserting at least a portion of said sleeve into said uterine cavity; and,
c. pushing out said elongate member from said sleeve within said uterine cavity, wherein said elongate member conforms into a predetermined three dimensional ball-like configuration within said uterine cavity following its emergence from said sleeve, thereby preventing expulsion from, malposition in said uterine cavity and perforation of uterine walls.

It is herein further disclosed that the aforementioned method further comprises steps of pushing out said elongate member, from said sleeve within said uterine cavity, such that said elongate member conforms into a predetermined three dimensional ball-like configuration within said uterine cavity on contact with the uterine fundus.

It is herein further disclosed that the aforementioned method further comprises steps of accommodating said elongate member within said sleeve prior to insertion into said uterine cavity.

It is herein further disclosed that the aforementioned method further comprises steps of configuring at least portion of said member such that after emergence of said member from said sleeve, said at least a portion is configured in a loop-like shape positioned opposite to the uterine fundus, thereby preventing perforation of the uterine walls.

It is herein further disclosed that the aforementioned method further comprises steps of configuring said member in a three dimensional configuration in a form selected from the group consisting of a ball-like, spherical-like, ovoid-like, globular-like, globe-like, orbicular-like and irregular form and any combination thereof.

It is herein further disclosed that the aforementioned method further comprises steps of configuring said member in a three dimensional configuration comprising a diameter which is significantly higher than the diameter of the cervical canal thereby preventing expulsion of said member from said uterine cavity.

It is herein further disclosed that the aforementioned method further comprises steps of configuring said member in a three dimensional configuration comprising a diameter of about 10 mm to about 15 mm.

It is herein further disclosed that the aforementioned method further comprises steps of additionally providing said member with a specialized conformation to facilitate prevention of undesirable side effects selected from the group consisting of perforation of the uterine walls and/or endometrium; expulsion from said uterine cavity, malposition of said member in said uterine cavity and any combination thereof.

It is herein further disclosed that the aforementioned method further comprises steps of selecting said conformation from the group consisting of a ball-like, sphere-like, globe-like, oval-like, egg-like, flange-like, lip-like, flattened-like, rounded-like, curved-like, flared-like and any combination thereof.

It is herein further disclosed that the aforementioned method further comprises steps of providing said member with an additional section to facilitate prevention of undesirable side effects selected from the group consisting of perforation of the uterine walls and/or endometrium, expulsion from said uterine cavity, malposition of said member in said uterine cavity and any combination thereof.

It is herein further disclosed that the aforementioned method further comprises steps of providing said section with a material with characteristics selected from the group consisting of soft, resilient, rubbery, elastic and a combination thereof.

It is herein further disclosed that the aforementioned method further comprises steps of providing at least a portion of said member with materials or coatings detectable by ultrasound monitoring.

It is herein further disclosed that the aforementioned method further comprises steps of providing at least a portion of said member with metal.

It is herein further disclosed that the aforementioned method further comprises steps of providing at least a portion of said member with polymeric materials.

It is herein further disclosed that the aforementioned method further comprises steps of providing at least a portion of said member with copper.

It is herein further disclosed that the aforementioned method further comprises steps of coating at least a portion of said member with copper.

It is herein further disclosed that the aforementioned method further comprises steps of selecting said metal from the group consisting of shape memory alloys, titanium, nickel, nitinol, stainless steel alloys, niobium, zirconium, cobalt-chrome alloys, molybdenum alloys, tungsten-rhenium alloys and any combination thereof.

It is herein further disclosed that the aforementioned method further comprises steps of providing at least partially of said member with elastic materials.

It is herein further disclosed that the aforementioned method further comprises steps of providing said member at its proximal end with a sphere-like conformation.

It is herein further disclosed that the aforementioned method further comprises steps of providing said sphere-like conformation with polyethylene and/or silicon materials.

It is herein further disclosed that the aforementioned method further comprises steps of removing said sleeve after said pushing out of said member from said sleeve within said uterine cavity.

It is herein further disclosed that the aforementioned method further comprises steps of further providing said IUB with insertion means.

It is herein further disclosed that the aforementioned method further comprises steps of providing said insertion means with a rod, longitudinally movable in said sleeve, said rod adapted for inserting said elongated member into said uterine cavity.

It is herein further disclosed that the aforementioned method further comprises steps of selecting said gynecological procedure or treatment from the group consisting of contraception, fertility treatment and pelvic inflammatory disease.

It is herein further disclosed that the aforementioned method further comprises steps of providing or coating at least a portion of said member with a drug releasing layer.

It is herein further disclosed that the aforementioned method further comprises steps of providing said drug releasing layer with a polymer.

It is herein further disclosed that the aforementioned method further comprises steps of providing said drug releasing layer with copper.

It is herein further disclosed that the aforementioned method further comprises steps of formulating said drug in a sustained release form.

It is herein further disclosed that the aforementioned method further comprises steps of formulating said drug release layer in a bolus release form.

It is herein further disclosed that the aforementioned method further comprises steps of facilitating the release of said drug into said intrauterine cavity in a uniform manner such that the concentration of said drug in said uterine cavity is uniform, thereby alleviating endometrial bleeding.

It is herein further disclosed that the aforementioned method further comprises steps of providing said drug releasing layer with hormones.

It is herein further disclosed that the aforementioned method further comprises steps of providing said drug releasing layer with antibiotic agents.

It is herein further disclosed that the aforementioned method further comprises steps of providing said drug releasing layer with analgesic agents.

It is herein further disclosed that the aforementioned method further comprises steps of selecting said hormone from the group consisting of progestogen, more specifically progesterone, estrogen and a combination thereof.

It is herein further disclosed that the aforementioned method further comprises steps of providing said drug releasing layer with a gonadotrophin hormone selected from the group consisting of FSH, a synthetic derivative of FSH, LH, a synthetic derivative of LH, and a combination thereof.

It is herein further disclosed that the aforementioned method further comprises steps of releasing said hormone from said drug releasing layer in a predetermined effective dose, thereby enhancing contraception.

It is herein further disclosed that the aforementioned method further comprises steps of releasing said hormone from said drug releasing layer in a predetermined effective dose, thereby reducing or alleviating symptoms selected from the group consisting of menstrual blood loss in a women having menorrhagia, postmenopausal symptoms and dysmenorrhea symptoms.

It is herein further disclosed that the aforementioned method further comprises steps of releasing said hormone from said drug releasing layer in a predetermined effective dose, thereby reducing the menstrual blood loss in women having menorrhagia.

It is herein further disclosed that the aforementioned method further comprises steps of releasing said hormones form said drug releasing layer in a predetermined effective dose for reducing postmenopausal symptoms.

It is herein further disclosed that the aforementioned method further comprises steps of releasing said hormones form said drug releasing layer in a predetermined effective dose for reducing dysmenorrhea symptoms.

It is herein further disclosed that the aforementioned method further comprises steps of releasing said gonadotrophin hormones form said drug releasing layer in a predetermined effective dose, thereby inducing ovulation.

It is herein further, disclosed that the aforementioned method further comprises steps of releasing said antibiotic agent form said drug releasing layer in a predetermined effective dose, thereby preventing pelvic inflammatory disease.

It is herein further disclosed that the aforementioned method further comprises steps of configuring at least a portion of said elongate member in a predetermined shape analogous to two ring-like or loop-like structures positioned approximately perpendicular or about 90 degrees to each other, so as to form a ball or spherical-like conformation, especially when said at least a portion of said member is fully released from said sleeve.

REFERENCES

1. "What are the most widely used contraceptive methods across the world?". Births/Birth control. Institut national d'études démographiques (INED). 2006. http://www.ined.fr/en/everything_about_population/faq/naissances_natalite/bd d/q_text/what_are_the_most_widely_used_contraceptive_methods_across_the_world_/question/80/. Retrieved on 2006 Nov.16.
2. World Health Organization (2002). "The intrauterine device (IUD)-worth singing about". Progress in Reproductive Health Research (60): 1-8. http://www.who.int/reproductive-health/hrp/progress/60/news60.html.
3. Lynch, Catherine M. "History of the IUD". Contraception Online. Baylor College of Medicine. http://www.contraceptiononline.org/meetings/IUD/lynch/presentation_text.cf m?cme_activityid=47&showmenu=1. Retrieved on 2006 Jul. 9.
4. "Evolution and Revolution: The Past, Present, and Future of Contraception". Contraception Online (Baylor College of Medicine) 10 (6). February 2000. http://www.contraceptiononline.org/contrareport/article01.cfm?art=93.
5. Bradley, Jeff (August 1998). "Ultrasound Interactive Case Study: Ring IUD". OBGYN.net. http://www.ob-gyn.net/us/us.asp?page=/us/present/9808/bradley. Retrieved on 2006 Jul. 9. (Has pictures of various IUD designs.)
6. Kaufman, J. (1993 May-June). "The cost of IUD failure in China". Studies in Family Planning 24 (3): 194-6. doi:10.2307/2939234. PMID 8351700.
7. IUDs-An Update. Chapter 2.3: Effectiveness.
8. Van Kets, H. E.; Editors C. Coll Capdevila, L. Iglesias Cortit and G. Creatsas (1997). "Importance of intrauterine contraception". Contraception Today, Proceedings of the 4th Congress of the European Society of Contraception. The Parthenon Publishing Group. 112-116. http://www.contrel.be/IUD%20GENERAL/Mhistory.htm. Retrieved on 2006 Jul. 9 (Has pictures of many IUD designs, both historic and modern.)
9. IUDs-An Update. Chapter 1: Background.
10. "Contraceptive coils (IUDs)". NetDoctor.co.uk. 2006. http://www.netdoctor.co.uk/sex_relationships/facts/contraceptivecoil.htm. Retrieved on 2006 Jul. 5.
11. French, R; Van Vliet H, Cowan F, et al. (2004). "Hormonally impregnated intrauterine systems (IUSs) versus other forms of reversible contraceptives as effective methods of preventing pregnancy". Cochrane Database of Systematic Reviews (3). doi:10.1002/14651858.CD001776.pub2. PMID 15266453.
12. Schering (May 13, 2003). "Nova T380 Patient information leaflet (PIL)". http://emc.medicines.org.uk/emc/assets/c/html/displaydoc.asp?documentid=36 41. Retrieved on 2007 Apr. 27.
13. IUDs—An Update. Chapter 2: Types of IUDs.
14. Smith (pseudonym), Sydney (Mar. 8, 2003). "Contraceptive Concerns". medpundit: Commentary on medical news by a practicing physician. http://www.medpundit.blogspot.com/2003_03_02_medpundit_archive.html. Retrieved on 2006 Jul. 16.
15. "Birth Control Options: The Progestasert Intrauterine Device (IUD)". Wyoming Health Council. 2004. http://wyhc.org/birth_control_options/Progestasert-IUD.php. Retrieved on 2006 Jul. 16.
16. IUDs—An Update. Chapter 2.5: Bleeding and Pain.
17. IUDs—An Update. Chapter 2.9: Ectopic Pregnancies.

18. "Mechanisms of the Contraceptive Action of Hormonal Methods and Intrauterine Devices (IUDs)". Family Health International. 2006. http://www.fhi.org/en/RH/Pubs/booksReports/methodaction.htm. Retrieved on 2006 Jul. 5.
19. Keller, Sarah (Winter 1996, Vol. 16, No. 2). "IUDs Block Fertilization". Network. Family Health International. http://www.fhi.org/en/RH/Pubs/Network/v16_2/nt1623.htm. Retrieved on 2006 Jul. 5.
20. IUDs—An Update. Worldwide Use—Developed Countries. Table 2: Worldwide Use of IUDs.

The invention claimed is:

1. An intra uterine device comprising an elongate conformable member with at least a portion including a contraceptive agent having shape memory adapted to conform into a predetermined three dimensional configuration formed by at least two loop-like structures approximately perpendicular with respect to each other when released from a hollow sleeve positioned within a uterine cavity, wherein a first plane defined within a first loop-like structure crosses through a second and approximately perpendicular plane defined within a second loop-like structure, and wherein said three dimensional configuration is capable of elastically contracting and expanding in response to contraction and expansion of said uterine cavity thereby enabling said three dimensional configuration to maintain its position within said uterine cavity, wherein the elongate conformable member has a proximal end and a caudal end and is configured to be linearized in the hollow sleeve into a single straight elongate conformable member having the proximal end at one end of the sleeve and the caudal end at the other end of the sleeve and is configured to be introduced from the sleeve into the uterine cavity to assume the predetermined three dimensional configuration.

2. The intra uterine device of claim 1, wherein said at least said portion having said shape memory is configured to fold into only two loop-like structures.

3. The intra uterine device of claim 2, wherein said elongate conformable member is composed of Nitinol.

4. The intra uterine device of claim 1, wherein said three dimensional configuration has a diameter of about 10 mm to about 15 mm.

5. The intra uterine device of claim 1, wherein said contraceptive agent is copper or a contraceptive hormone.

6. The intra uterine device of claim 1, wherein said three dimensional configuration facilitates release of said contraceptive agent into said intrauterine cavity in a uniform manner.

7. The intra uterine device of claim 1, wherein the device consists essentially of the elongate conformable member and wherein the three-dimensional configuration is ball-like in shape.

8. A method of contraception comprising: (a) providing an elongate conformable member including at least a portion having a shape memory adapted to conform into a predetermined three dimensional configuration formed by at least two loop-like structures approximately perpendicular with respect to each other, wherein a first plane defined within a first loop-like structure crosses through a second and approximately perpendicular plane defined within a second loop-like structure, said elongate member including a contraceptive agent, wherein the elongate conformable member has a proximal end and a caudal end; and (b) delivering said elongate member through a hollow sleeve into a uterine cavity to thereby form said three dimensional configuration in said uterine cavity wherein the elongate conformable member is linearized into a single straight elongate conformable member in the hollow sleeve with the proximal end at one end of the sleeve and the caudal end at the other end of the sleeve and introduced proximal-end first from the sleeve into the uterine cavity to assume the predetermined three dimensional configuration; wherein said three dimensional configuration is capable of elastically contracting and expanding in response to contraction and expansion of said uterine cavity thereby enabling said three dimensional configuration to maintain its position within said uterine cavity and release said contraceptive agent therein.

9. The method according to claim 8, wherein one loop-like structure is positioned opposite a uterine fundus following emergence of said elongate member from said hollow sleeve.

10. The method of claim 8, wherein said three dimensional configuration has a diameter of about 10 mm to about 15 mm.

* * * * *